(12) United States Patent
Butler

(10) Patent No.: US 10,052,210 B2
(45) Date of Patent: Aug. 21, 2018

(54) HEIGHT ADJUSTABLE SPINAL PROSTHESES

(71) Applicant: Life Spine, Inc., Huntley, IL (US)

(72) Inventor: Michael S. Butler, St. Charles, IL (US)

(73) Assignee: Life Spine, Inc., Huntley, IL (US)

(*) Notice: Subject to any disclaimer, the term of this patent is extended or adjusted under 35 U.S.C. 154(b) by 195 days.

(21) Appl. No.: 14/991,270

(22) Filed: Jan. 8, 2016

(65) Prior Publication Data

US 2016/0120652 A1 May 5, 2016

Related U.S. Application Data

(63) Continuation of application No. 12/079,670, filed on Mar. 29, 2008, now Pat. No. 9,237,954.

(Continued)

(51) Int. Cl.
*A61F 2/44* (2006.01)
*A61F 2/30* (2006.01)

(52) U.S. Cl.
CPC .......... *A61F 2/44* (2013.01); *A61F 2/30744* (2013.01); *A61F 2002/3055* (2013.01); *A61F 2002/30133* (2013.01); *A61F 2002/30235* (2013.01); *A61F 2002/30492* (2013.01); *A61F 2002/30507* (2013.01); *A61F 2002/30525* (2013.01); *A61F 2002/30601* (2013.01); *A61F 2002/30616* (2013.01); *A61F 2002/30777* (2013.01);

(Continued)

(58) Field of Classification Search
CPC ....................................... A61F 2/44

USPC ............... 623/17.11, 17.15, 17.16; 600/238; 254/95–103
See application file for complete search history.

(56) References Cited

U.S. PATENT DOCUMENTS

| 5,664,762 A * | 9/1997 | Rothbauer ............... B66F 3/10 254/101 |
| 6,524,341 B2 | 2/2003 | Lang et al. |

(Continued)

*Primary Examiner* — David Isabella
*Assistant Examiner* — Christine Nelson
(74) *Attorney, Agent, or Firm* — Foley & Lardner LLP

(57) ABSTRACT

Dimensionally adjustable spinal prostheses are adjustable in an axial or superior to inferior dimension such that spinal prostheses may assume variations in height. The height adjustable spinal prostheses are characterized by first and second portions that are configured for adjustable coupling with one another. Spatial adjustment between the first and second portions is provided by an adjustment assembly. The adjustment mechanism preferably, but not necessarily, provides infinite adjustment over a minimum prosthesis height to a maximum prosthesis height. In one form, first and second ends of the height adjustable spinal prostheses are configured to receive an endplate. The endplates aid in attachment and/or anchoring of the spinal prosthesis within the spine. The endplates may be fashioned in various configurations such as circular or anatomical. In one form, the adjustment assembly utilizes rotational motion for varying the axial position of one prosthetic portion relative to the other prosthetic portion. Rotational movement of an adjustment mechanism of the adjustment assembly is translated into axial movement of one prosthetic portion relative to the other prosthetic portion. In another form, the adjustment mechanism is a screw and gearing assembly. In yet another form, the adjustment mechanism is a rack and pinion assembly.

18 Claims, 9 Drawing Sheets

Related U.S. Application Data

(60) Provisional application No. 60/920,699, filed on Mar. 29, 2007.

(52) U.S. Cl.
CPC ............... *A61F 2002/30841* (2013.01); *A61F 2002/4475* (2013.01); *A61F 2220/0025* (2013.01); *A61F 2230/0015* (2013.01); *A61F 2230/0069* (2013.01); *A61F 2310/00017* (2013.01); *A61F 2310/00023* (2013.01)

(56) References Cited

U.S. PATENT DOCUMENTS

| | | | |
|---|---|---|---|
| 6,752,832 B2 * | 6/2004 | Neumann | A61F 2/44 606/247 |
| 6,808,538 B2 * | 10/2004 | Paponneau | A61F 2/44 623/17.16 |
| 2004/0049271 A1 | 3/2004 | Biedermann et al. | |
| 2004/0059271 A1 | 3/2004 | Berry | |
| 2004/0133279 A1 | 7/2004 | Krueger et al. | |
| 2006/0004447 A1 | 1/2006 | Mastrorio et al. | |
| 2006/0058877 A1 | 3/2006 | Gutlin et al. | |
| 2006/0058879 A1 | 3/2006 | Metz-Stavenhagen | |
| 2006/0136062 A1 | 6/2006 | Dinello et al. | |
| 2006/0200244 A1 | 9/2006 | Assaker | |
| 2006/0241770 A1 | 10/2006 | Rhoda et al. | |
| 2007/0049943 A1 | 3/2007 | Moskowitz et al. | |
| 2007/0059149 A1 | 3/2007 | Rich | |
| 2007/0255415 A1 | 11/2007 | Edie et al. | |
| 2008/0015704 A1 | 1/2008 | Gradl et al. | |
| 2008/0133013 A1 | 6/2008 | Duggal et al. | |

* cited by examiner

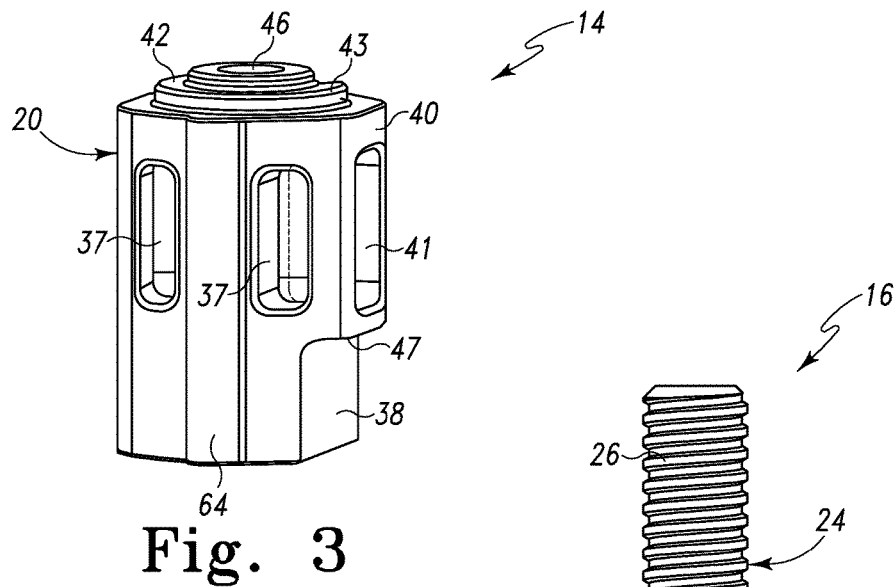
Fig. 3
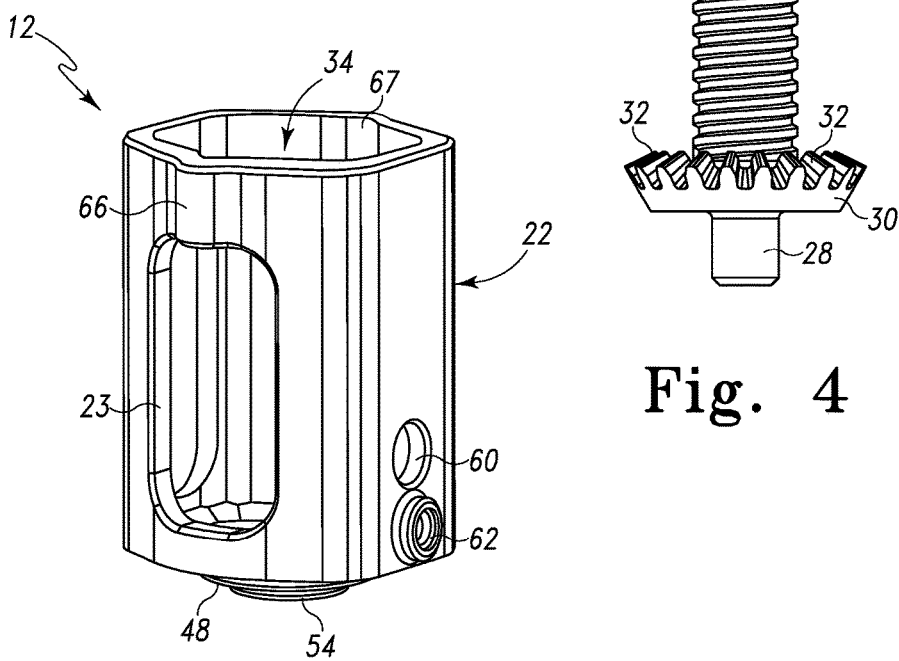
Fig. 4
Fig. 2

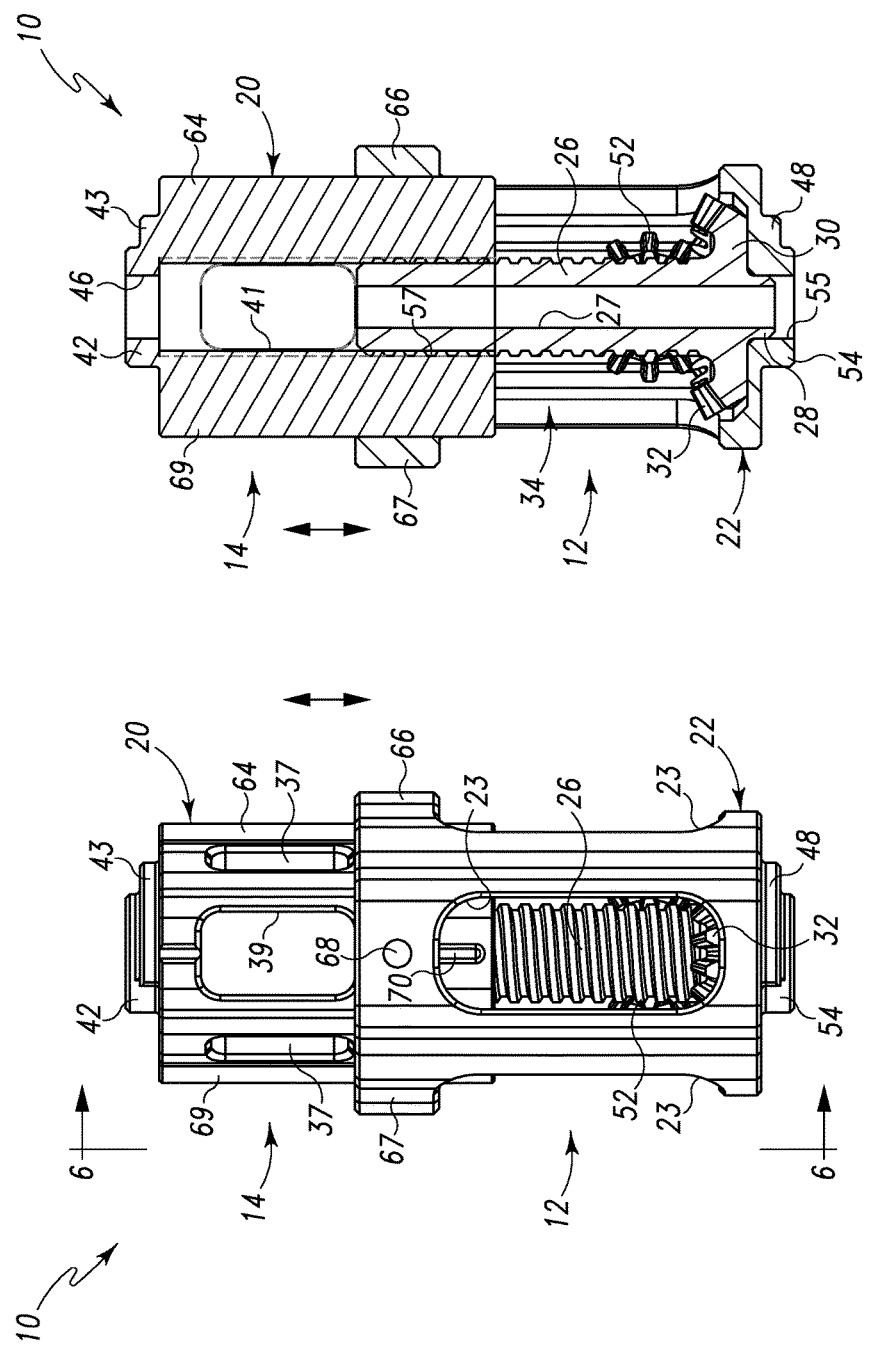

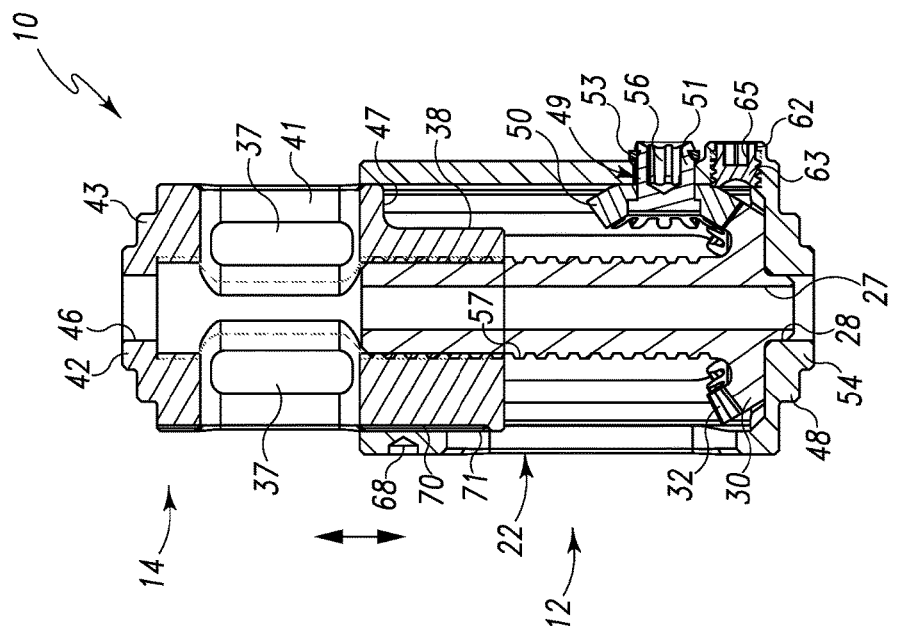
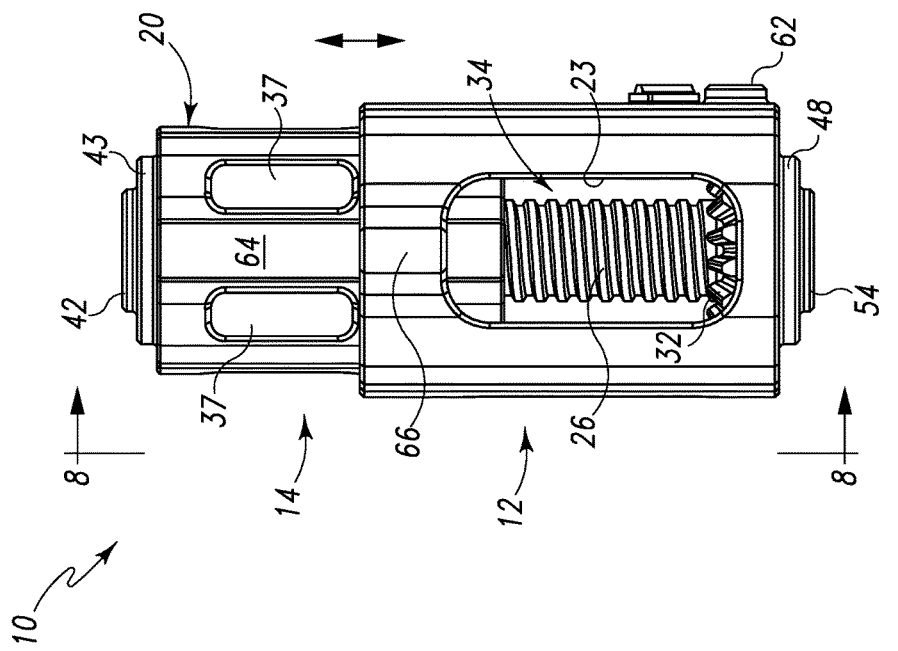

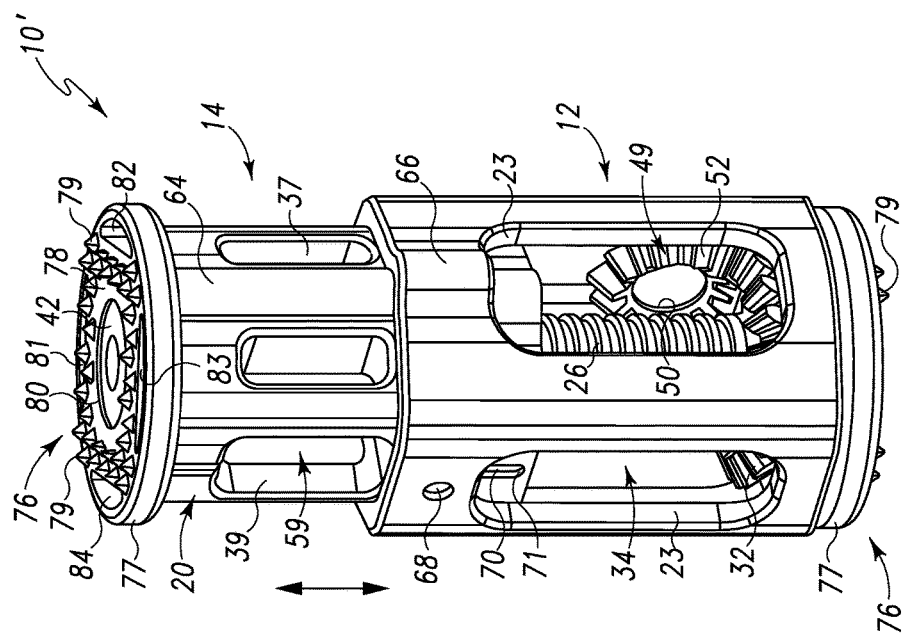
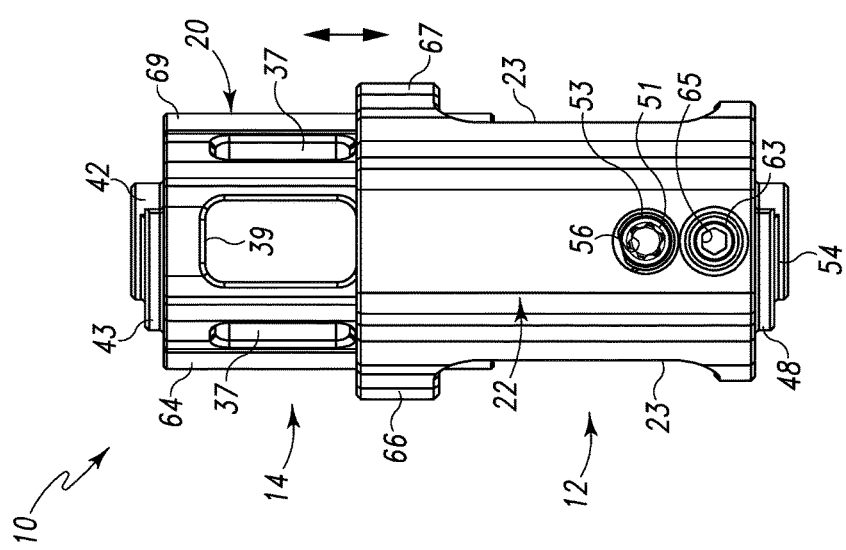
Fig. 10
Fig. 9

HEIGHT ADJUSTABLE SPINAL PROSTHESES

CROSS-REFERENCE TO RELATED APPLICATIONS

This patent application is a continuation of U.S. patent application Ser. No. 12/079,670, filed Mar. 29, 2008, entitled "Height Adjustable Spinal Prostheses," which claims the benefit of and/or priority to U.S. Provisional Patent Application Ser. No. 60/920,699 filed Mar. 29, 2007, entitled "Height Adjustable Spinal Prosthesis," both of which are incorporated herein by reference in their entireties.

BACKGROUND OF THE INVENTION

Field of the Invention

The present invention relates to relates to spinal prostheses and, more particularly, to dimensionally adjustable spinal prostheses.

Background Information

Vertebrae and/or discs of a human spine can sometimes be damaged due to disease or injury, may be malformed through a congenital defect or can simply deteriorate due to age. In other cases, vertebrae and/or discs may become fractured, compressed or otherwise damaged. In these and other situations the vertebrae and/or discs can cause an undesired and/or abnormal curvature of the spine with respect to lordosis or kyphosis.

Because of this, orthopedic surgery may be utilized to replace one or more vertebrae or discs with a spinal prosthesis or one or more vertebrae may be repaired via kyphoplasty or vertebroplasty. In the case of disc replacement, the spinal prosthesis may be used between adjacent vertebrae in order to provide proper spacing of the vertebrae. A spinal prosthesis may also be used to promote fusion between adjacent vertebrae. When so utilized, bone or bone fusion material is often placed about or in the spinal prosthesis in order to promote growth of bone between the adjacent vertebrae.

One type of spinal prosthesis may also be used in place of a vertebra or a vertebra and adjacent disc. The vertebra and disc are removed. This type of spinal prosthesis is then placed between remaining adjacent vertebrae as the middle vertebra has been removed. When this is the case, the adjacent discs may also be removed.

When such spinal prostheses are used, it is desirable for them to engage as much surface of the vertebral bone as possible in order to provide support to the bone and to thereby reduce the likelihood of subsidence of the device into the bone resulting from contact pressure of the prosthesis against vertebral bone surfaces. Subsidence can occur since part of the vertebral bone is somewhat spongy in nature, especially near the centers of the adjacent vertebrae.

Because anatomical relationships for each patient are different, it is desirable to have a spinal prosthesis that may be varied in various dimensions. One such aspect is the height or axial (superior/inferior) length of the spinal prosthesis. As such, it is desirable to provide a spinal prosthesis that is dimensionally adjustable in height. Accordingly, there presently exists a need for height adjustable spinal prostheses.

SUMMARY OF THE INVENTION

The present invention provides height adjustable spinal prostheses. The height adjustable spinal prostheses may be used as vertebral prostheses, vertebral body replacement (VBR) prostheses, and/or spinal distraction prosthesis as appropriate. Other uses are contemplated.

The spinal prostheses are adjustable in an axial or superior to inferior dimension (height) such that spinal prostheses may assume variations in height. Such height variation may be accomplished in situ.

The present height adjustable spinal prostheses are characterized by first and second prosthetic portions that are configured in adjustable coupling with one another to effect height variation. Either prosthetic portion may be adjusted relative to the other prosthetic portion or both may be adjusted. Spatial adjustment between the prosthetic portions is provided by an adjustment assembly.

In one form, the prosthetic portions are adjustably coupled for axial displacement relative to one another or of one relative to the other in order to effect overall prosthesis height variation. The adjustment mechanism preferably, but not necessarily, provides infinite adjustment over a minimum prosthesis height to a maximum prosthesis height.

In one form, first and second ends of the height adjustable spinal prostheses are configured to receive an endplate. The endplates aid in attachment and/or anchoring of the spinal prosthesis within the spine. The endplates may be fashioned in various configurations such as circular or anatomical.

In one form, the adjustment assembly utilizes rotational motion for varying the axial position of one prosthetic portion relative to the other prosthetic portion. Rotational movement of an adjustment mechanism of the adjustment assembly is translated into axial movement of one prosthetic portion relative to the other prosthetic portion.

In one form, the adjustment mechanism is a screw and gearing assembly. In another form, the adjustment mechanism is a rack and pinion assembly.

The present modular height adjustable spinal prostheses may be implanted anteriorly, transversly and/or posteriorlaterally.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein:

FIG. 2 is a perspective view of a lower portion of the height adjustable spinal prosthesis of FIG. 1;

FIG. 3 is a perspective view of an upper portion of the height adjustable spinal prosthesis of FIG. 1;

FIG. 4 is a front view of a height adjustment portion of the height adjustable spinal prosthesis of FIG. 1;

FIG. 5 is a first side view of the height adjustable spinal prosthesis of FIG. 1;

FIG. 6 is a sectional view of the height adjustable spinal prosthesis of FIG. 5 taken along line 6-6 thereof;

FIG. 7 is a second side view of the height adjustable spinal prosthesis of FIG. 1;

FIG. 8 is a sectional view of the height adjustable spinal prosthesis of FIG. 7 taken along line 8-8 thereof;

FIG. 9 is a third side view of the height adjustable spinal prosthesis of FIG. 1;

FIG. 10 is a perspective view of the height adjustable spinal prosthesis of FIG. 1 with endplates thereon;

Like reference numerals indicate the same or similar parts throughout the several figures.

Figure 1:
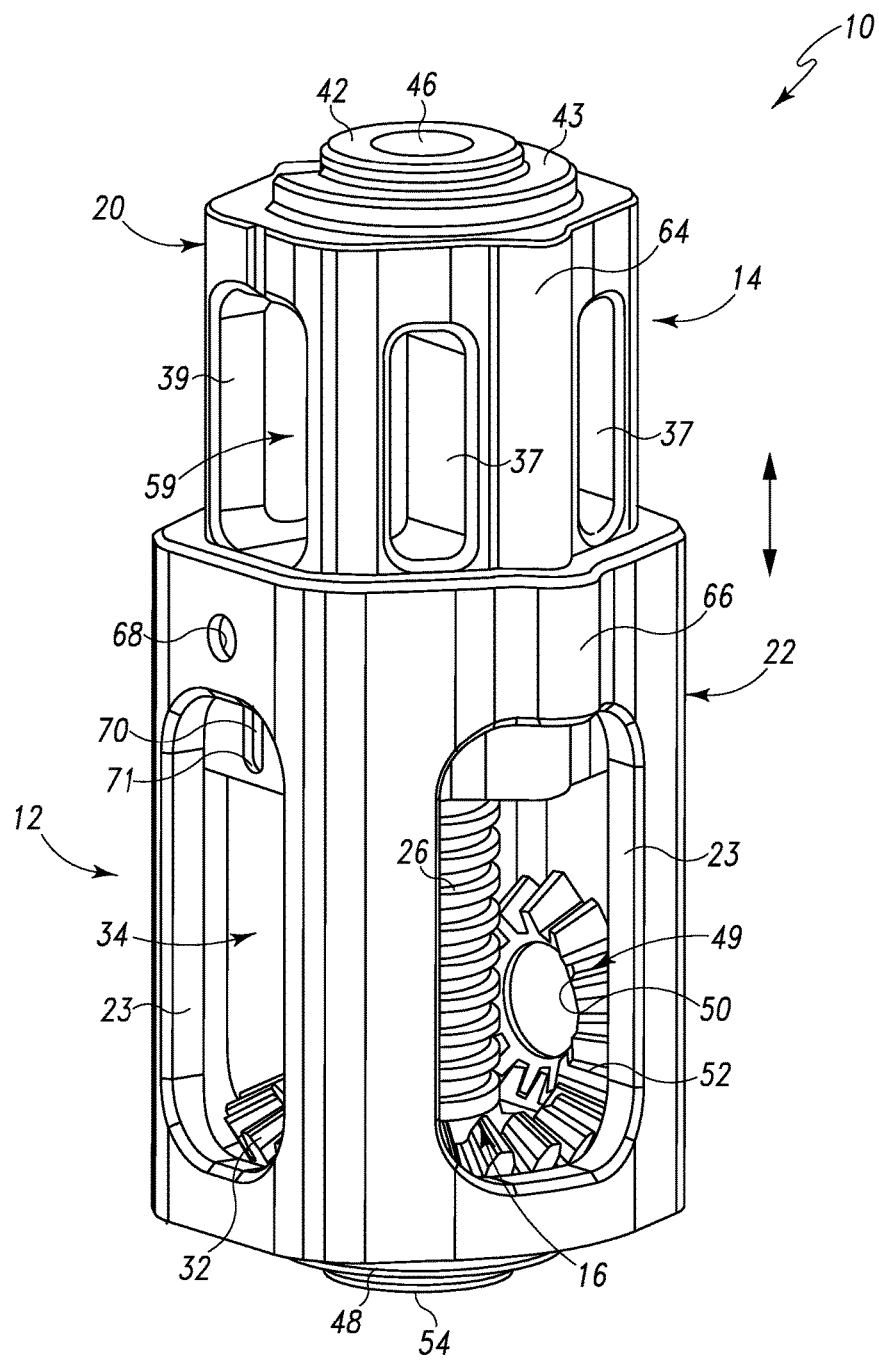
FIG. 1 is a perspective view of an exemplary embodiment of a height adjustable spinal prosthesis fashioned in accordance with the present principles.

A detailed description of the features, functions and/or configuration of the components depicted in the various figures will now be presented. It should be appreciated however that not all of the features of the components of the figures are necessarily described. Some of these non discussed features as well as discussed features are inherent from the figures. Other non discussed features may be inherent in component geometry and/or configuration.

DETAILED DESCRIPTION OF EMBODIMENTS OF THE INVENTION

Referring to the figures and in particular FIGS. 1-9, there is depicted an exemplary embodiment of a height adjustable, adjustable height and/or dynamic spinal prosthesis or implant, generally designated 10, fashioned in accordance with the present principles. Height is axial or superior/inferior dimension of the prostheses when implanted in the spine. The height adjustable spinal prosthesis 10 is characterized by components fabricated from a bio-compatible material such as stainless steel, titanium, a titanium alloy, composite, polymer or any combination thereof. It should be appreciated that the height adjustable spinal prosthesis 10 is for use as a vertebral prosthesis, a vertebral body replacement (VBR), a spinal distraction device and/or a fusion device as appropriate. It should be further appreciated that the height adjustable spinal prosthesis 10 may be fabricated in various sizes as appropriate to accommodate different anatomy sizes.

The height adjustable spinal prosthesis 10 is characterized by a lower or arbitrarily first prosthetic portion or assembly 12 (hereinafter and collectively, lower portion 12), an upper or arbitrarily second portion or assembly 14 (hereinafter and collectively, upper portion 14) and an adjustment portion or assembly 16. In accordance with the principles of the present invention, one prosthetic portion is movable relative to the other prosthetic portion and particularly, but not necessarily, are axially movable relative to one another. In the present embodiment, the upper portion 14 is axially movable relative to the lower portion 12 through rotation of the height adjustment assembly 16 thereby providing adjustment in height of the spinal prosthesis 10. Particularly, the upper portion 14 is axially movable, displaceable or translatable relative to the lower portion 12 through rotation of the height adjustment assembly 16 such that the overall height of the spinal prosthesis 10 is adjustable from a minimum prosthesis height to a maximum prosthesis height depending on dimensions of the components. The terms upper and lower are in relation to the preferred, but not necessary, implantation orientation of the prostheses as implanted into the spine, the head or the person being upper and the feet being the lower.

FIG. 2 depicts the lower portion 12 of the spinal prosthesis 10 of FIG. 1. The lower portion 12 is defined by a polygonal body 22 having an open top or upper end and a closed bottom or lower end enclosing and defining an interior space or chamber 34 that opens into a threaded central shaft 41 of the body 22 (see e.g. FIGS. 6 and 8). Various sides of the body 22 have an elongated opening 23. The elongated opening 23 provides access to the interior 34 of the body 22. If desired, bone growth material may be received into the interior 34 via one or more of the openings 23 after assembly. The body 22 has first and second axial guides 66 and 67 in the walls of the body and opposite one another. Each guide 66, 67 comprises an axial formation that defines an inner axial channel. Each axial channel corresponds to and receives an axial projection 64 and 69 of the upper portion 14. These features create and define an anti-rotation structure for the spinal prosthesis and particularly the upper portion relative to the lower portion. The upper portion 14 is restrained from rotation relative to the lower portion 12 so that rotational motion from the adjustment portion 16 is translated into axial or up/down movement of the upper portion 14 relative to the lower portion 12. Particularly, when the screw shaft 26 of the adjustment portion 16 rotates in the threaded bore 57 of the upper portion 14 (see, e.g., FIGS. 6 and 8), the rotational motion is translated into axial or up/down motion of the upper portion 16 relative to the lower portion 12.

The body 22 also includes a bore 60 on one side thereof and a port 62 situated in the side thereof and axially below the bore 60. An input or bevel assembly 49 utilizes the bore 60 (see, e.g. FIG. 8). The input bevel assembly 49 includes a polylobular or configured input socket 56 (see, e.g., FIG. 9) by which the adjustment assembly 16 is actuated. A polylobular or configured driving tool is utilized to rotate the input bevel assembly 49. Rotation of the input bevel assembly 49 rotates the adjustment portion 16 to raise and lower the height of the spinal prosthesis 10. The port 62 is preferably threaded and thus adapted to receive a threaded set pin or key 63 (see, e.g., FIG. 8). The threaded set pin 63 is utilized to prevent rotation of the input bevel gear 50 of the input bevel assembly 49 by extending into the teeth 52 of the input bevel gear 50 when threaded into the port 62. The threaded set pin 63 includes a hex or configured input socket 65 (see, e.g., FIG. 9) that receives a hex or configured driving tool to set the set pin 63 as appropriate.

The lower end of the body 22 further includes a hub 54 having an axial bore 55 therethrough (see, e.g. FIGS. 6 and 8) that extends from the lower end. A collar 48 partially surrounds or extends about the hub 54. The collar 48 controls angular freedom of end plates (see, e.g. FIGS. 11-14) of and/or for the spinal prosthesis 10. A bore 68 is defined in the body 22 that is configured to project into the interior 34 for cooperation with the slot 70.

FIG. 3 depicts the upper portion 14 of the spinal prosthesis 10 of FIG. 1. The upper portion 12 is disposed in the interior 34 and is configured to axially move within the interior 34 in order to adjust the overall height of the spinal prosthesis 10. The upper portion 14 is defined by a generally polygonal body 20 having a hub 42 having an axial bore 46 therethrough (see, e.g. FIG. 8) that extends from the upper end thereof. A collar 43 partially surrounds or extends about the hub 42. The collar 43 controls angular freedom of end plates (see, e.g. FIGS. 11-14) of and/or for the spinal prosthesis 10. Various sides of the body 20 have ovoid openings 37, 39 and 41. If desired, bone growth material may be received into one or more of the openings 37, 39 and 41. The body 20 has first and second axial guides 64 and 69 in the opposite walls of the body 20. The axial guides 64, 69 correspond with guides 66 and 67 of the lower portion 12 and co-act as described above. The body 20 also has a cutout area that defines a projection 40, an undersurface or ledge 47 of the projection 40 and a flat 38. As best seen in FIG. 8, the cutout area The projection 40 and flat 38 are sized such that when the upper portion 12 is at its lowest axial position and intermediate positions within the cavity 34 of the lower portion 14, the upper portion 12 will not interfere with the bevel assembly 49 of the lower portion 14 (see, e.g. FIG. 8).

Referring particularly to FIG. 4, the height adjustment portion 16 is characterized by a body 24 that defines an externally threaded shaft 26, a bevel gear 30 and an end or seating shaft 28. The body 24 is preferably, but not necessarily, unitary. The threaded shaft 26 extends axially from one side thereof in one direction from the center of the bevel gear 30 while the seating shaft 28 extends axially from an opposite side thereof in an opposite direction from the center of the bevel gear 30. The bevel gear 30 includes a plurality of teeth 32. The number and spacing of the teeth 32 is matched to the number and spacing of teeth 52 of a bevel gear 50 of the adjustment assembly such that the bevel gears 30 and 50 mesh. As best seen in FIGS. 6 and 8, the body 24 includes an axial bore 27 that extends through the threaded shaft 26, the bevel gear 30 and the seating shaft 28 thereby forming a cannula that extends axially from on end of the body 24 to the other.

As best seen in FIGS. 6 and 8, the body 20 includes a threaded bore 57 into which is received the threaded shaft 26 of the adjustment portion 16. In order to prevent withdrawal of upper portion 14 from the lower portion 12, the lower portion 12 includes the bore/stake 68 that extends radially inward. The upper portion 14 includes a slot 70 terminating in a stop 71. The stake 68 extends into the slot 70 such that the upper portion 14 is confined in axial movement by the stake 68 within the slot 70. When the upper portion 12 reaches its maximum upward height or position, the stake 68 abuts the stop 71 thereby preventing further upward movement of the upper portion 12.

The adjustment assembly may include the adjustment portion 16 and the input bevel assembly 49. The bevel assembly 49 is disposed in the lower portion and particularly in and accessible by the bore 60. The bevel assembly 49 includes a D-shaped shaft 51 that is borne in bore 60 and also retains a bevel gear 50. The input bevel assembly shaft 51 is fixed in rotational translation externally to the lower body 20 by a C-retaining ring 53 (see, e.g. FIG. 8). The bevel gear 50 meshes with the bevel gear 30 of the adjustment portion 16. The bevel gear 50 is offset 90° from the bevel gear 30. The shaft 51 further has a hex input bore 65 that is configured to accept a hex driver. Other configurations may be used. Rotation of the shaft 51 via a hex driver rotates the bevel gear 50 which rotates the threaded shaft 26. Because the upper portion 14 is fixed against rotation as described above, rotation of the threaded shaft 26 causes the axial translation or movement of the upper portion 14 relative to the lower portion 12. Rotation of the bevel assembly 49 in one direction causes the rotation of the adjustment portion 16 in one direction causing axial movement or translation of the upper portion 14 relative to the lower portion 12 in one direction while rotation of the bevel assembly 49 in an opposite direction causes the rotation of the adjustment portion 16 in an opposite direction causing axial movement or translation of the upper portion 14 relative to the lower portion 12 in an opposite direction. Thus, the upper portion 14 may be made to move up and down. Upward movement of the upper portion 14 relative to the lower portion 12 increases the height of the spinal prosthesis 10. Because the adjustment is provided via a screw, there is infinite height adjustment from a minimum to a maximum.

Figure 11:
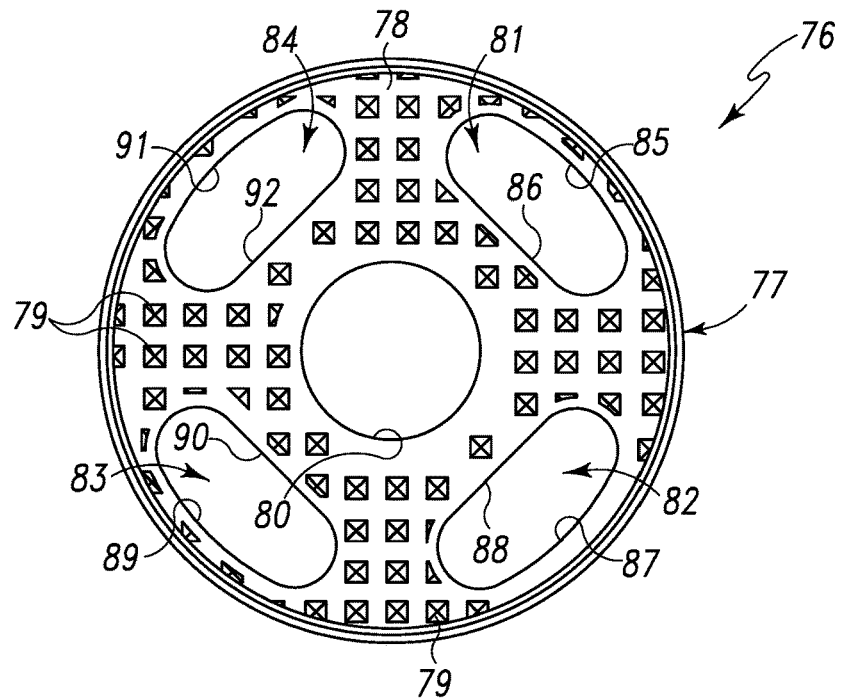
FIG. 11 is an embodiment of an exemplary circular endplate for the height adjustable spinal prosthesis of FIG. 1.

Referring to FIG. 11, there is depicted an exemplary embodiment of an endplate 76 for use with the spinal prosthesis 10. The endplate 76 is defined by a circular body 77 and may come in various sizes. The endplate 76 is configured to be received (press fit) onto the upper and lower ends 42 and 54 of the upper portion 14 and the lower portion 12 respectively and to abut and/or be in contact with a vertebra. As such, the body 77 has a center bore 80 that is sized to be received on upper and lower ends 42 and 54 of the upper portion 14 and the lower portion 12, respectively. The body 77 further has four generally oval cutouts 81, 82, 83 and 84 that radially surround the center bore 80. The cutouts 81, 82, 83 and 84 are spaced equidistant about the center bore 80, but not necessarily so. The generally oval cutout 81 has a generally curved edge 85 proximate the periphery of the body 77 and a generally straight edge 86 proximate the center bore 80. This is shown in greater detail in FIG. 13 with respect to the endplate 94 of FIG. 12. Likewise, the generally oval cutout 82 has a generally curved edge 87 proximate the periphery of the body 77 and a generally straight edge 88 proximate the center bore 80. Likewise, the generally oval cutout 83 has a generally curved edge 89 proximate the periphery of the body 77 and a generally straight edge 90 proximate the center bore 80. Likewise the generally oval cutout 84 has a generally curved edge 91 proximate the periphery of the body 77 and a generally straight edge 92 proximate the center bore 80. Moreover, the upper surface 78 of the body 77 includes a plurality of spikes 79 that aid in seating the endplate 76 on the vertebra.

Figure 12:
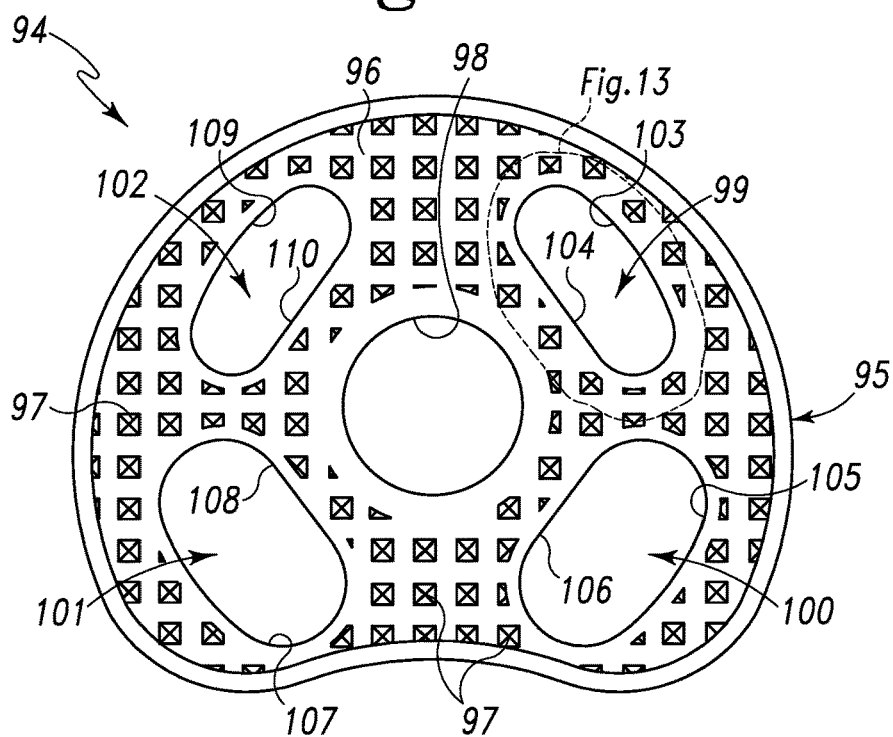
FIG. 12 is an embodiment of an exemplary anatomical endplate for the height adjustable spinal prosthesis of FIG. 1.
Figure 13:
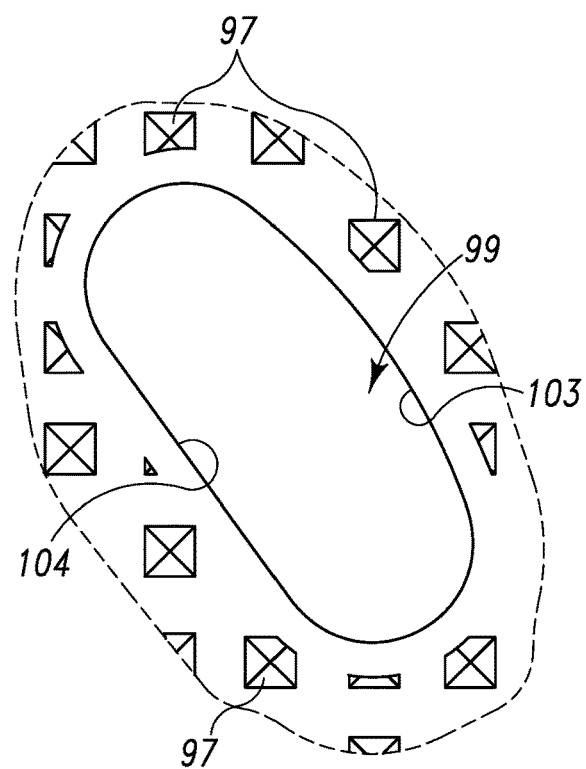
FIG. 13 is an enlarged portion of an area of the anatomical endplate of FIG. 12 labeled FIG. 13 in FIG. 12.

Referring to FIGS. 12 and 13, there is depicted another exemplary embodiment of an endplate 94 for use with the spinal prosthesis 10. The endplate 94 is defined by a generally kidney-shaped body 95 and may come in various sizes. and may come in various sizes. The endplate 94 is configured to be received (press fit) onto the upper and lower ends 42 and 54 of the upper portion 14 and the lower portion 12 respectively and to abut and/or be in contact with a vertebra. As such, the body 94 has a center bore 98 that is sized to be received on upper and lower ends 42 and 54 of the upper portion 14 and the lower portion 12, respectively. The body 95 further has four generally oval cutouts 99, 100, 101 and 102 that radially surround the center bore 98. The cutouts 99, 100, 101 and 102 are spaced equidistant about the center bore 98, but not necessarily so. As best seen in FIG. 13, the generally oval cutout 99 has a generally curved edge 103 proximate the periphery of the body 95 and a generally straight edge 104 proximate the center bore 98. This is shown in greater detail in FIG. 13. Likewise, the generally oval cutout 100 has a generally curved edge 105 proximate the periphery of the body 95 and a generally straight edge 106 proximate the center bore 98. Likewise, the generally oval cutout 101 has a generally curved edge 107 proximate the periphery of the body 95 and a generally straight edge 108 proximate the center bore 98. Likewise the generally oval cutout 102 has a generally curved edge 109 proximate the periphery of the body 95 and a generally straight edge 110 proximate the center bore 98. Moreover, the upper surface 96 of the body 95 includes a plurality of spikes 97 that aid in seating the endplate 94 on the vertebra.

Figure 14:
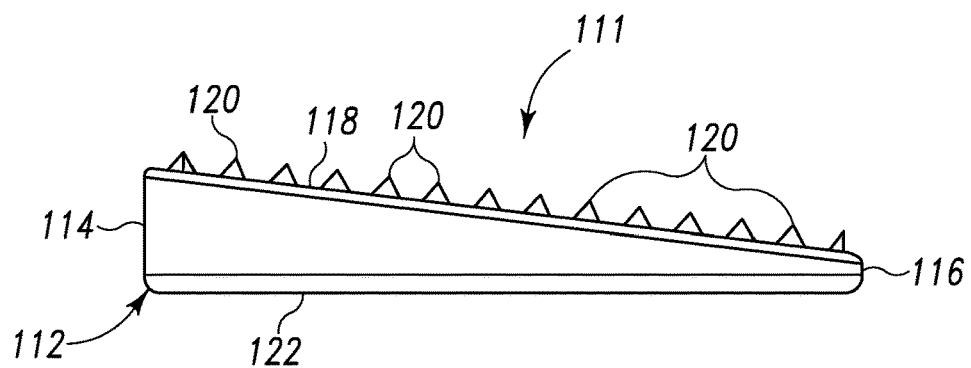
FIG. 14 is a side view of an endplate for the height adjustable spinal prosthesis of FIG. 1 particularly showing its slope or angle between an end of the endplate and a front of the endplate, the endplate representative of all endplates for the height adjustable spinal prosthesis of FIG. 1.

Referring to FIG. 14 there is depicted a side view of an endplate 111 having a body 112 that is representative of endplates 76 and 94. As such the body 112 has an upper surface 120 and a lower surface 122. The upper surface 120 includes a plurality of spikes 120. FIG. 14 particularly shows the angularity from one side 114 to another side 116 of the body 112. The endplate 111 may be made having one of various angles. It is contemplated that an endplate may come in five (5) different angles: −3.5°, 0°, 3.5°, 7° and 10.5°. Other angles may be used.

FIG. 10 depicts a modular height adjustable spinal prosthesis generally designated 10'. The spinal prosthesis 10' is characterized by the height adjustable spinal prosthesis 10 and endplates—here being round endplates 76. As it can be seen, one endplate 76 is disposed on the hub 42 of the upper portion 14 while another endplate 76 is disposed on the hub 54 of the lower portion 12. The center bores of the endplates are sized to accordingly fit onto the hubs. While a flat or 0° angle endplate is shown for the spinal prosthesis 10', it should be understood that angled endplates may be used. The endplates 76 are also situated on the respective collars so as to be flat.

Figure 15:
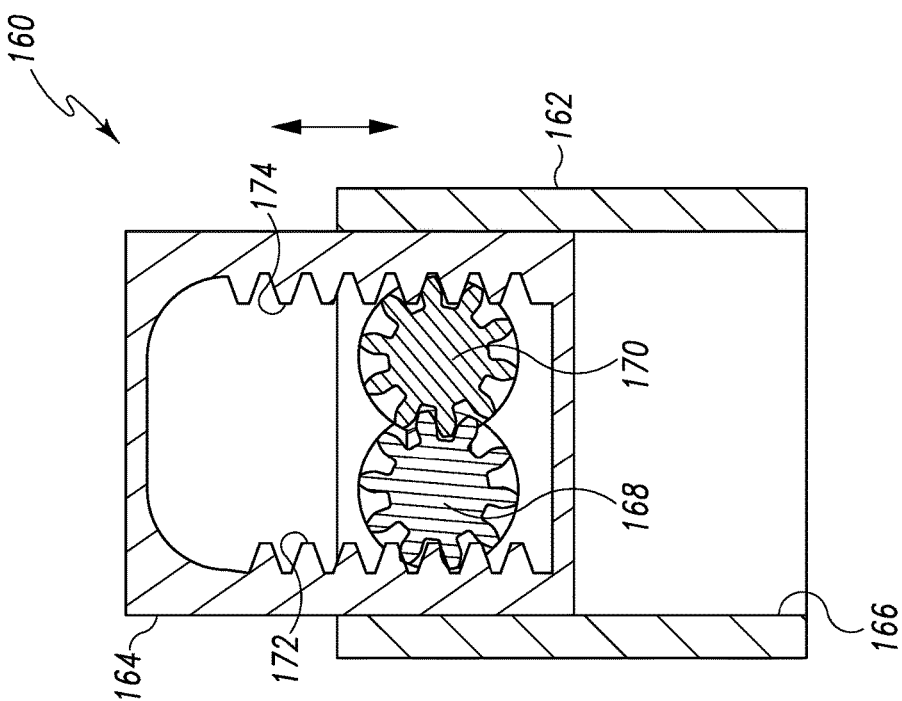
FIG. 15 is a side sectional view of an exemplary embodiment of a rack and pinion type height adjustable spinal prosthesis fashioned in accordance with the present principles.

Referring to FIG. 15 there is depicted another exemplary embodiment of a height adjustable, adjustable height and/or dynamic spinal prosthesis generally designated 160 fashioned in accordance with the principles of the present invention. The spinal prosthesis 160 may be considered a rack and pinion style or type of height adjustable spinal prosthesis. The height adjustable spinal prosthesis 160 is characterized by components fabricated from a biocompatible material such as stainless steel, titanium, a titanium alloy, composite, polymer or the like. It should be appreciated that the height adjustable spinal prosthesis 160 is for use as a vertebral prosthesis, a vertebral body replacement (VBR), a spinal distraction device and/or a fusion device as appropriate. It should be further appreciated that the height adjustable spinal prosthesis 160 may be fabricated in various sizes as appropriate to accommodate different anatomy sizes.

The spinal prosthesis 160 is characterized by a lower body or portion 162 and an upper body or portion 164. The lower and upper bodies 162, 164 are generally cylindrical. The upper body 164 is axially adjustable relative to the lower body 162. In this manner the spinal prosthesis 160 is height adjustable. The lower body 162 has an internal bore 166 in which the upper body 164 is disposed. The lower body 162 has two pinions 168, 170 that are constrained in translation such that they only rotate. The upper body 164 has twin racks 172, 174 on sidewalls thereof that mesh respectively with the pinions 168, 170. Rotation of the pinions 168, 170 in one direction causes the upper body 164 to axially move or translate in one direction relative to the lower body 162 while rotation of the pinions 168, 170 in an opposite direction causes the upper body 164 to axially move or translate in an opposite direction relative to the lower body 162. Upward translation of the upper body 164 relative to the lower body 162 increases the height of the spinal prosthesis 160. The rack and pinion adjustment provides infinite height adjustment from a minimum height to a maximum height.

Figure 16:
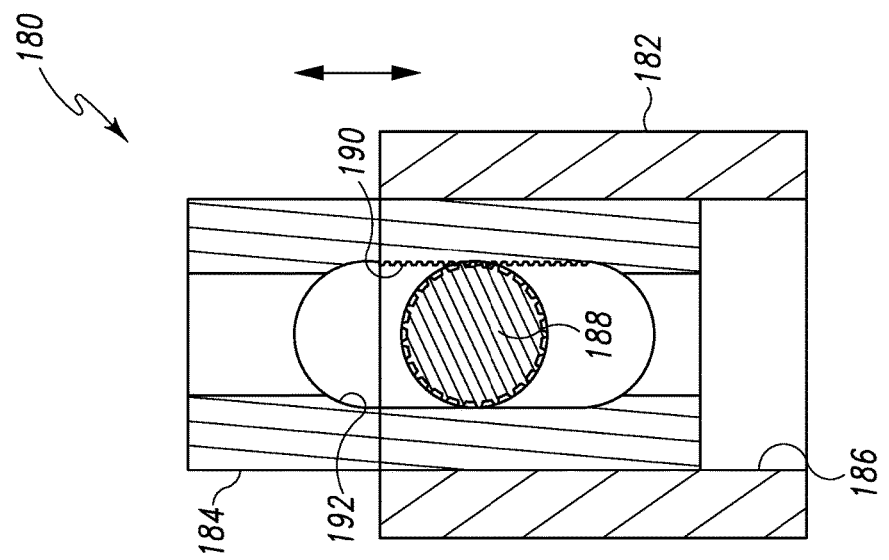
FIG. 16 is a side sectional view of another exemplary embodiment of a rack and pinion type height adjustable spinal prosthesis fashioned in accordance with the present principles.

Referring to FIG. 16 there is depicted another exemplary embodiment of a height adjustable, adjustable height and/or dynamic spinal prosthesis generally designated 180 fashioned in accordance with the principles of the present invention. The spinal prosthesis 180 may be considered a rack and pinion style or type of height adjustable spinal prosthesis. The height adjustable spinal prosthesis 180 is characterized by components fabricated from a biocompatible material such as stainless steel, titanium, a titanium alloy, composite, polymer or the like. It should be appreciated that the height adjustable spinal prosthesis 180 is for use as a vertebral prosthesis, a vertebral body replacement (VBR), a spinal distraction device and/or a fusion device as appropriate. It should be further appreciated that the height adjustable spinal prosthesis 180 may be fabricated in various sizes as appropriate to accommodate different anatomy sizes.

The spinal prosthesis 180 is characterized by a lower body or portion 182 and an upper body or portion 184. The lower and upper bodies 182, 184 are generally cylindrical. The upper body 184 is axially adjustable relative to the lower body 182. In this manner the spinal prosthesis 180 is height adjustable. The lower body 182 has an internal bore 186 in which the upper body 184 is disposed. The lower body 182 has a pinion 188 that is constrained in translation such that it only rotates. The upper body 184 has a rack 190 on one sidewall thereof that meshes respectively with the pinion 188. Rotation of the pinion 188 in one direction causes the upper body 184 to axially move or translate in one direction relative to the lower body 182 while rotation of the pinion 188 in an opposite direction causes the upper body 184 to axially move or translate in an opposite direction relative to the lower body 182. Upward translation of the upper body 184 relative to the lower body 182 increases the height of the spinal prosthesis 180. The rack and pinion adjustment provides infinite height adjustment from a minimum height to a maximum height.

Figure 17:
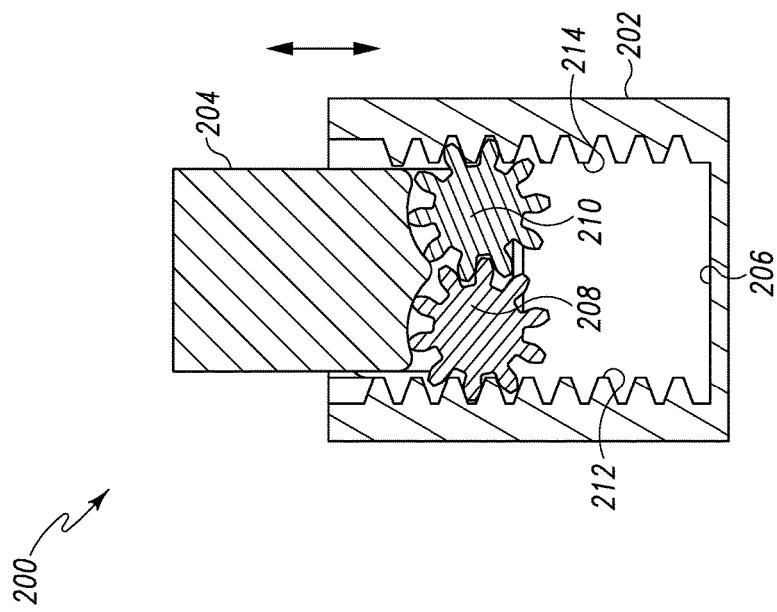
FIG. 17 is a side sectional view of another exemplary embodiment of a rack and pinion type height adjustable spinal prosthesis fashioned in accordance with the present principles.

Referring to FIG. 17 there is depicted another exemplary embodiment of a height adjustable, adjustable height and/or dynamic spinal prosthesis generally designated 200 fashioned in accordance with the principles of the present invention. The spinal prosthesis 200 may be considered a rack and pinion style or type of height adjustable spinal prosthesis. The height adjustable spinal prosthesis 200 is characterized by components fabricated from a biocompatible material such as stainless steel, titanium, a titanium alloy, composite, polymer or the like. It should be appreciated that the height adjustable spinal prosthesis 200 is for use as a vertebral prosthesis, a vertebral body replacement (VBR), a spinal distraction device and/or a fusion device as appropriate. It should be further appreciated that the height adjustable spinal prosthesis 200 may be fabricated in various sizes as appropriate to accommodate different anatomy sizes.

The spinal prosthesis 200 is characterized by a lower body or portion 202 and an upper body or portion 204. The lower and upper bodies 202, 204 are generally cylindrical. The upper body 204 is axially adjustable relative to the lower body 202. In this manner the spinal prosthesis 200 is height adjustable. The lower body 202 has an internal bore 206 in which the upper body 204 is disposed. The upper body 202 has two pinions 208, 210 that are constrained in translation such that they only rotate. The lower body 204 has twin racks 212, 214 on sidewalls thereof that mesh respectively with the pinions 208, 210. Rotation of the pinions 208, 210 in one direction causes the upper body 204 to axially move or translate in one direction relative to the lower body 202 while rotation of the pinions 208, 210 in an opposite direction causes the upper body 204 to axially move or translate in an opposite direction relative to the lower body 202. Upward translation of the upper body 204 relative to the lower body 202 increases the height of the spinal prosthesis 200. The rack and pinion adjustment provides infinite height adjustment from a minimum height to a maximum height.

Figure 18:
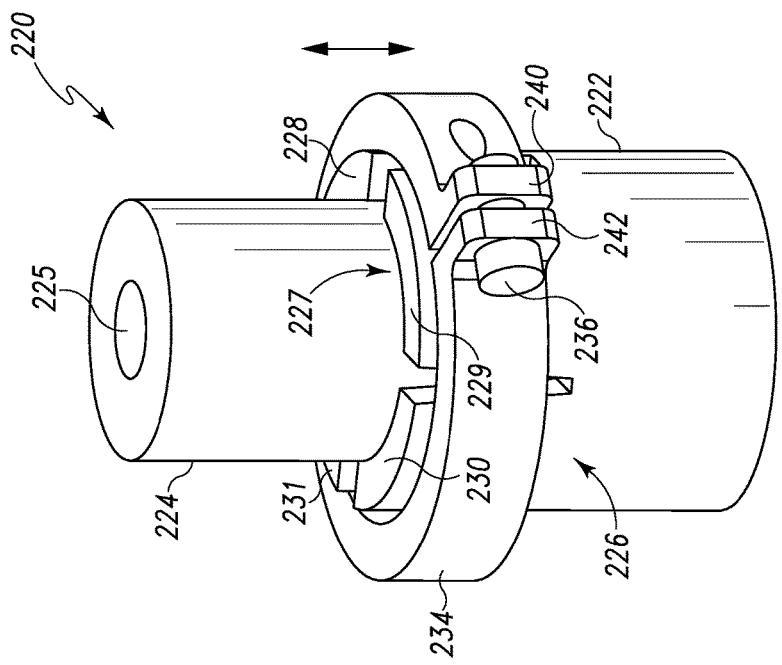
FIG. 18 is a perspective view of an exemplary embodiment of another height adjustable spinal prosthesis fashioned in accordance with the present principles.

Referring to FIG. 18 there is depicted another exemplary embodiment of a height adjustable, adjustable height and/or dynamic spinal prosthesis generally designated 220 fashioned in accordance with the principles of the present invention. The spinal prosthesis 220 may be considered a clamp style or type of height adjustable spinal prosthesis. The height adjustable spinal prosthesis 220 is characterized by components fabricated from a bio-compatible material such as stainless steel, titanium, a titanium alloy, composite, polymer or the like. It should be appreciated that the height adjustable spinal prosthesis 220 is for use as a vertebral prosthesis, a vertebral body replacement (VBR), a spinal distraction device and/or a fusion device as appropriate. It should be further appreciated that the height adjustable spinal prosthesis 220 may be fabricated in various sizes as appropriate to accommodate different anatomy sizes.

The spinal prosthesis 220 is characterized by a lower body or portion 222 and an upper body or portion 224. The lower and upper bodies 222, 224 are generally cylindrical. The upper body 224 is axially adjustable relative to the lower body 222. In this manner the spinal prosthesis 220 is height adjustable. The lower body 222 has a collet 226 defining a bore 227 surrounded by four (4) flanges 228, 229, 230 and 231. The upper body 224 has an axial bore 225 and is situated in the bore 227 of the lower body 222. A clamp or band 234 surrounds the flanges 228, 229, 230 and 231 and is tightened by a screw 236 extending through threaded flanges 240 and 242 thereof. Axial fixation of the upper body 224 in and relative to the lower body 222 is achieved by tightening the clamp 234 about the flanges 228, 229, 230 and 231 such that the flanges 228, 229, 230 and 231 move radially inward. Height adjustment is thus accomplished by positioning the upper body 224 within and relative to the collet 226 and tightening the clamp 234.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spinal prosthesis comprising:
a first prosthetic portion having a body defining an interior chamber, wherein the body includes a first hub extending from the body and a first collar extending axially between the body and the first hub, the first collar only partially surrounding the first hub;
a second prosthetic portion at least partially received in the interior chamber of the first prosthetic portion, the second prosthetic portion axially displaceable relative to the first prosthetic portion, wherein the second prosthetic portion includes a body, wherein the body of the second prosthetic portion includes a second hub extending from the body and a second collar extending axially between the body and the second hub, the second collar only partially surrounding the second hub;
an adjustment mechanism coupled to the first and second prosthetic portions within the bodies of the first and second prosthetic portions and operable to effect axial displacement of the second prosthetic portion relative to the first prosthetic portion;
a first end plate received on the first hub and situated on the first collar of the first prosthetic portion; and
a second end plate received on the second hub and situated on the second collar of the second prosthetic portion;
wherein the first collar is structured to control an angular freedom of the first end plate; and
wherein the second collar is structured to control an angular freedom of the second end plate.

2. The spinal prosthesis of claim 1, wherein the second prosthetic portion includes a projection extending from the body that defines a cutout.

3. The spinal prosthesis of claim 2, wherein the cutout at least partially receives at least a portion of the adjustment mechanism when the second prosthetic portion is at a minimum axial displacement distance relative to the first prosthetic portion, and wherein the cutout provides a relatively larger gap between the first prosthetic portion and the second prosthetic portion than in a surrounding region between the second prosthetic portion and the first prosthetic portion in the interior chamber when the first and second prosthetic portions are coupled together.

4. The spinal prosthesis of claim 1, wherein the adjustment mechanism utilizes rotational motion to effect axial displacement of the second prosthetic portion relative to the first prosthetic portion.

5. The spinal prosthesis of claim 4, wherein the adjustment mechanism includes a screw shaft and an input bevel gear operable to rotate perpendicular to and in a meshing relationship with the screw shaft for effecting the rotational motion.

6. An implantable spinal prosthesis comprising:
a first prosthetic portion having a body defining an interior chamber;
a second prosthetic portion adapted for reception in the interior chamber of the first prosthetic portion, the second prosthetic portion axially displaceable relative to the first prosthetic portion, wherein engagement of the first prosthetic portion and the second prosthetic portion permit a relative longitudinal sliding movement; and
an adjustment mechanism coupled to the first and second prosthetic portions and operable to effect axial displacement of the second prosthetic portion relative to the first prosthetic portion, wherein the adjustment mechanism utilizes rotational motion for effecting axial displacement of the second prosthetic portion relative to the first prosthetic portion, and wherein the adjustment mechanism comprises:
a screw shaft disposed in the interior chamber and rotatably coupled to the second prosthetic portion,
an input bevel gear disposed in the interior chamber, rotatably coupled to the first prosthetic portion, and adapted to rotate perpendicular to and in a meshing relationship with the screw shaft, and
a threaded set pin extending through a port in the body of the first prosthetic portion and adjacent to the first bore, the threaded set pin structured to selectively engage and prevent rotation of the input bevel gear to prevent further axial displacement of the second prosthetic portion relative to the first prosthetic portion.

7. The implantable spinal prosthesis of claim 6,
wherein the first prosthetic portion further includes a first hub and a first collar that only partially surrounds the first hub, the first collar extending axially between the body of the first prosthetic portion and the first hub; and
wherein the second prosthetic portion further includes a second hub and a second collar that only partially surrounds the second hub, the second collar extending axially between the body of the second prosthetic portion and the second hub.

8. The implantable spinal prosthesis of claim 7, further comprising:
a first end plate received on the first hub and situated on the first collar of the first prosthetic portion; and
a second end plate received on the second hub and situated on the second collar of the second prosthetic portion;
wherein the first collar is structured to control an angular freedom of the first end plate, and wherein the second collar is structured to control an angular freedom of the second end plate.

9. The implantable spinal prosthesis of claim 8,
wherein the first hub is cylindrical in shape;
wherein the second hub is cylindrical in shape;
wherein the first end plate has a central bore that is press fit with the cylindrical first hub; and
wherein the second end plate has a central bore that is press fit with the cylindrical second hub.

10. The implantable spinal prosthesis of claim 6,
wherein the second prosthetic portion further includes a projection extending from the body and defining a cutout, wherein the cutout at least partially receives the input bevel gear when the second prosthetic portion is at a minimum axial displacement distance relative to the first prosthetic portion; and
wherein the cutout defines a relatively larger gap between the first prosthetic portion and the second prosthetic portion than in a surrounding region between the first prosthetic portion and the second prosthetic portion in the interior chamber when the first and second prosthetic portions are coupled together.

11. A spinal prosthesis comprising:
a first prosthetic portion having a body, the body defining an interior chamber;
a second prosthetic portion adapted for axial displacement within the interior chamber of the first prosthetic portion relative to the first prosthetic portion whereby height of the spinal prosthesis is varied, the second prosthetic portion having a body and a projection extending from the body that defines a cutout;
an adjustment mechanism coupled to the first and second prosthetic portions and operable to effect axial displacement thereof;
wherein the cutout at least partially receives at least a portion of the adjustment mechanism when the second prosthetic portion is at a minimum axial displacement distance relative to the first prosthetic portion, and wherein the cutout defines a relatively larger gap between the first prosthetic portion and the second prosthetic portion than in a surrounding region between the second prosthetic portion and the first prosthetic portion in the interior chamber when the first and second prosthetic portions are coupled together.

12. The spinal prosthesis of claim 11, wherein the body of the second prosthetic portion defines an opening to provide access to the interior chamber, wherein the interior chamber and the opening are configured to receive bone growth material.

13. The spinal prosthesis of claim 11,
wherein the first prosthetic portion further includes a first hub and a first collar that only partially surrounds the first hub, the first collar extending axially between the body of the first prosthetic portion and the first hub; and
wherein the second prosthetic portion further includes a second hub and a second collar that only partially surrounds the second hub, the second collar extending axially between the body of the second prosthetic portion and the second hub.

14. The spinal prosthesis of claim 13,
wherein the first hub is cylindrical in shape;
wherein the second hub is cylindrical in shape;
wherein the first end plate has a central bore that is press fit with the cylindrical first hub; and
wherein the second end plate has a central bore that is press fit with the cylindrical second hub.

15. The spinal prosthesis of claim 14, wherein the cutout at least partially receives the input bevel gear when the second prosthetic portion is at a minimum axial displacement distance relative to the first prosthetic portion.

16. The spinal prosthesis of claim 11, wherein the adjustment mechanism includes:
a bevel assembly having a configured input socket extending at least partially through the first bore in the first prosthetic portion, and an input bevel gear coupled to the input socket and disposed in the interior chamber, the input socket and input bevel gear having a first rotational axis perpendicular to a longitudinal axis of the interior chamber;
a bevel gear ninety degrees offset from the input bevel gear and disposed in the interior chamber, the bevel gear having a second rotational axis perpendicular to the first rotational axis;
a threaded shaft extending from the bevel gear and coupled to the threaded bore of the second prosthetic portion; and
a threaded set pin configured to engage the input bevel gear and prevent further axial displacement of the second prosthetic portion relative to the first prosthetic portion;
wherein rotation of the input socket rotates the input bevel gear about the first rotational axis, which rotates the bevel gear about the second rotational axis, which rotates the threaded shaft, which effects axial displacement of the second prosthetic portion relative to the first prosthetic portion.

17. The spinal prosthesis of claim 11,
wherein the body of the first prosthetic portion includes a wall contour defining a first axial guide;
wherein the body of the second prosthetic portion includes a wall contour defining a second axial guide;
where the first axial guide is structured to receive the second axial guide to permit relative longitudinal sliding movement and inhibit relative rotational movement between the second prosthetic portion and the first prosthetic portion.

18. The spinal prosthesis of claim 11, wherein the adjustment mechanism utilizes rotational motion to effect axial displacement of the second prosthetic portion relative to the first prosthetic portion.

* * * * *